(12) United States Patent
Kumar et al.

(10) Patent No.: US 10,258,811 B2
(45) Date of Patent: Apr. 16, 2019

(54) AUDIO-VISUAL SUMMARIZATION SYSTEM FOR RT PLAN EVALUATION

(71) Applicant: KONINKLIJKE PHILIPS N.V., Eindhoven (NL)

(72) Inventors: Prashant Kumar, Bangalore (IN); Vaitheeswaran Ranganathan, Bangalore (IN); Karl Antonin Bzdusek, Madison, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 403 days.

(21) Appl. No.: 14/772,441

(22) PCT Filed: Mar. 11, 2014

(86) PCT No.: PCT/IB2014/059607
§ 371 (c)(1),
(2) Date: Sep. 3, 2015

(87) PCT Pub. No.: WO2014/147511
PCT Pub. Date: Sep. 25, 2014

(65) Prior Publication Data
US 2016/0030767 A1  Feb. 4, 2016

Related U.S. Application Data

(60) Provisional application No. 61/803,212, filed on Mar. 19, 2013.

(51) Int. Cl.
*A61N 5/10* (2006.01)

(52) U.S. Cl.
CPC .......... *A61N 5/1031* (2013.01); *A61N 5/103* (2013.01); *A61N 5/1071* (2013.01); *A61N 2005/1074* (2013.01)

(58) Field of Classification Search
CPC .... A61N 5/103; A61N 5/1031; A61N 5/1071; A61N 2005/1074
See application file for complete search history.

(56) References Cited

U.S. PATENT DOCUMENTS

| 4,455,609 A | 6/1984 | Inamura et al. |
| 2005/0254622 A1* | 11/2005 | Llacer .................. A61N 5/1031 378/65 |

(Continued)

FOREIGN PATENT DOCUMENTS

| JP | 2008178619 | | 8/2008 | |
| WO | 2005035061 A2 | | 4/2005 | |
| WO | WO 2011024085 | * | 3/2011 | ............... A61N 5/10 |

Primary Examiner — Carrie R Dorna

(57) ABSTRACT

A method for reviewing a treatment plan (24) for delivering radiation therapy to a patient. The treatment plan (24) includes geometric analysis data, dose distribution analysis data, dose volume histogram data, parametric analysis data or deliverability analysis data of a patient. First, for the treatment plan (24), a plurality of clinical and delivery goals are identified (20, 22). Next, goal data points are extracted (26) from the treatment plan (24). Then, data points are correlated (28) to identify deficiencies in the treatment plan (24). A report is generated (30) to display on a display (10) the correlated data points using visual markings (84) to highlight identified deficiencies. Text and audio notations can be attached to the report to explain the correlations and warn a user of plan deficiencies.

18 Claims, 5 Drawing Sheets

(56) References Cited

U.S. PATENT DOCUMENTS

| | | | |
|---|---|---|---|
| 2007/0127623 A1* | 6/2007 | Goldman | A61N 5/1031 378/65 |
| 2007/0156453 A1* | 7/2007 | Frielinghaus | A61N 5/103 705/2 |
| 2010/0049549 A1 | 2/2010 | Nelms | |
| 2010/0054413 A1* | 3/2010 | Sobering | A61N 5/1031 378/65 |
| 2010/0086183 A1 | 4/2010 | Vik et al. | |
| 2012/0157746 A1 | 6/2012 | Meltsner et al. | |
| 2014/0161339 A1* | 6/2014 | Wakai | G06T 7/0012 382/131 |

* cited by examiner

AUDIO-VISUAL SUMMARIZATION SYSTEM FOR RT PLAN EVALUATION

CROSS REFERENCE TO RELATED APPLICATIONS

This application is a national filing of PCT application Serial No. PCT/IB2014/059607, filed Mar. 11, 2014, published as WO 2014/147511 A1 on Sep. 25, 2014, which claims the benefit of U.S. provisional application Ser. No. 61/803,212 filed Mar. 19, 2013, which is incorporated herein by reference.

The present application relates to the medical arts and finds particular application with radiation treatment planning and will be described with particular reference thereto. However, it is to be appreciated that it will also find application in other medical interventions and treatment procedures. When a patient is diagnosed with cancer, several treatment options can be pursued. One treatment option is radiation therapy. When radiation therapy is selected, a detailed plan is constructed from large amounts of data about the patient.

In the past decade, technological advancements have provided a big leap in the field of intensity modulated radiation therapy (IMRT), intensity modulated proton therapy (IMPT) and the like, to improve dose delivery. Recently the research interest has shifted towards methods of automating various tasks involved in plan generation, starting from beam placement to dose optimization, to assist and reduce the workload burden on the clinical user.

With respect to plan evaluation, most of the focus has had been on quantitative metrics which can qualify the effectiveness of the therapy plan. However, various aspects of the plan evaluation process are subjective. The clinical user manually collects or visualizes all these pieces of information to judge the quality of the plan. The plan includes a vast array of information sources and data from those sources. The clinical user will find great use in improving the efficiency of plan evaluation process by assisting the clinical user with meaningful and quick information about the plan.

Plan evaluation is classified into three phases: 1. Physical evaluation, 2. Technical evaluation and 3. Clinical evaluation. The physical and technical aspects of a plan are generally examined by a technician after the completion of the plan. The clinical aspects of a plan are investigated by a radiation oncologist. Currently an IMRT plan is evaluated based on five categories that cover the physical, technical and clinical aspects of a plan: 1. Geometric analysis, 2. Dose distribution analysis, 3. Dose Volume Histogram (DVH) analysis, 4. Parametric analysis and 5. Deliverability analysis.

The geometric analysis is performed to evaluate the optimality of beams placement. Beam placement is a very important step. The quality of optimization is mainly influenced by the number of beams and their angles. Rules have been formulated for optimal beam placement in IMRT in view of increasing the optimality and deliverability of an IMRT plan.

The dose distribution analysis qualitatively verifies the optimality of dose distribution in axial, coronal and saggital planes. This analysis can be further split up into 2D analysis and 3D analysis. 2D dose distribution analysis implies the evaluation of dose distribution slice-by-slice. This type of analysis is used to evaluate the conformality of the prescribed dose with respect to the target volume in each slice. This type of analysis can also reveal the distribution of cold or hot spots in and around the target volume. Cold or hot spots are areas within the target and organs at risk that receive less or greater than the intended dose of radiation. The 3D distribution analysis is useful in perceiving how conformal a dose distribution is to the overall target volume with respect to a set of beam orientations.

Dose Volume Histograms (DVH) are a powerful tool for evaluating the optimality of a plan. A DVH represents a 3-dimensional dose distribution in a graphical 2-dimensional format. A DVH for target volume graphically represents the quality of the dose distribution in terms of coverage, conformity and homogeneity. The DVH curves for Organs-at-risk (OARs) represent the efficiency at which the OARs are spared in terms of mean and maximum dose.

The parametric analysis is performed to quantitatively verify the optimality of dose. The parameters used in this analysis are: (a) minimum, mean and maximum dose for target volume and OARs and (b) coverage, conformity and homogeneity indices for target volume. Apart from physical metrics for plan evaluation, a plurality of biological metrics are used in plan evaluation. These biological metrics include Equivalent Uniform Dose (EUD), Tumor Control Probability (TCP) and Normal Tissue Complication Probability (NTCP) and the like.

Deliverability analysis is performed in order to evaluate how robust the plan is in terms of dose delivery. This analysis involves the verification of parameters such as number of segments, minimum or average monitor units (MU) per segment, Minimum Segment Area (MSA), total delivery time and the like. MU is a measure of machine output of a linear accelerator in radiation therapy. The deliverability analysis reveals whether a plan is actually deliverable or not.

Radiation treatment plan (RTP) evaluation is a time consuming process which also requires expertise. A systematic approach to automatically guide the user through various evaluation aspects can make the process more robust and less time consuming. Treatment plan evaluation is an extensive process, which requires physicists and oncologists to spend large amounts of time in examining the quality and deliverability of a treatment plan. A plan might get underestimated or overestimated if the users are not given sufficient amount of time for plan evaluation. The clinical user needs to collect distributed pieces of information by navigating through various sections of a planning application. The various analysis sources can be hard to organize into a coherent plan as the sources are all related to one another to form a complete treatment plan.

With innumerable data sources attributed to creating a treatment plan for each patient, proper evaluation of the plan must be conducted to assure that the treatment goals and priorities are met to best treat the patient. However, evaluating the plan according to the various sources of data can be difficult and subjective. An objective evaluation of a treatment plan will be useful to oncologists, physicists, and other clinicians, in determining whether goals are met. It will also be useful for highlighting the parts of the plan where treatment goals are failed or are useful in evaluating or redesigning the plan. A compiled report would significantly aid the patient's doctors in evaluating the plan to meet the treatment goals.

In accordance with one preferred method of the present application, a method for evaluating treatment plans for delivering radiation therapy to a patient is provided, the method includes: capturing evaluation parameters for a treatment plan, the plan comprising patient specific data; extracting important/related data from the patient specific data according to the captured evaluation priorities/parameters; and generating a summary associated with the plan, the summary presenting the extracted data.

In accordance with a preferred embodiment of the present application, a system for evaluating a radiation treatment plan is provided. A user interface receives an input from a user. A processor is programmed to: extract related data points from the patient specific data according to the input received from the user; correlate the extracted data from different data sources; and generate a summary of the extracted data.

In accordance with another preferred method of the present application, a method for reviewing a treatment plan for delivering radiation therapy to a patient, the method comprising: identifying a plurality of clinical goals for a treatment plan, the treatment plan having a plurality of data points from a plurality of analysis sources; identifying a plurality of delivery goals for the treatment plan; extracting important data points from the plurality of analysis sources; correlating related extracted data points, the correlated data points are correlated from different analysis sources of the plurality of analysis sources; and generating a report to display the correlated data points.

One advantage of the present application resides in automation of a significant amount of plan evaluation.

Another advantage resides in automatically finding the relevant data when presented with the clinical or delivery goals of a radiation therapy plan.

Another advantage resides in not overlooking data which a user performing a manual plan evaluation might.

Another advantage resides in warning the users of plan deficiencies relative to the plan goals.

Still further advantages will be appreciated by those of ordinary skill upon understanding the application.

The figures are only for purposes of illustrating one or more embodiments and are not to be taken as limiting.

The present application provides functionality to objectively evaluate a radiation treatment plan. The application provides functionality to accept clinical or delivery goals from user input or a stored set of standardized goals. The application provides functionality to store and access treatment plan data specific to a patient, where the data is comprised of multiple distributed sources. It also provides for extracting relevant pieces of data according to the specified goals of the plan. It further provides functionality to correlate the extracted data points with the specified goals of the plan. It provides functionality to generate a unique patient and plan specific report to display the correlations with highlights distinctly showing the correlation and the feasibility of the plan according to the goals. The report can also include text and audio notations, and multiple screens to form a video clip that can be shown to the user.

Figure 1:
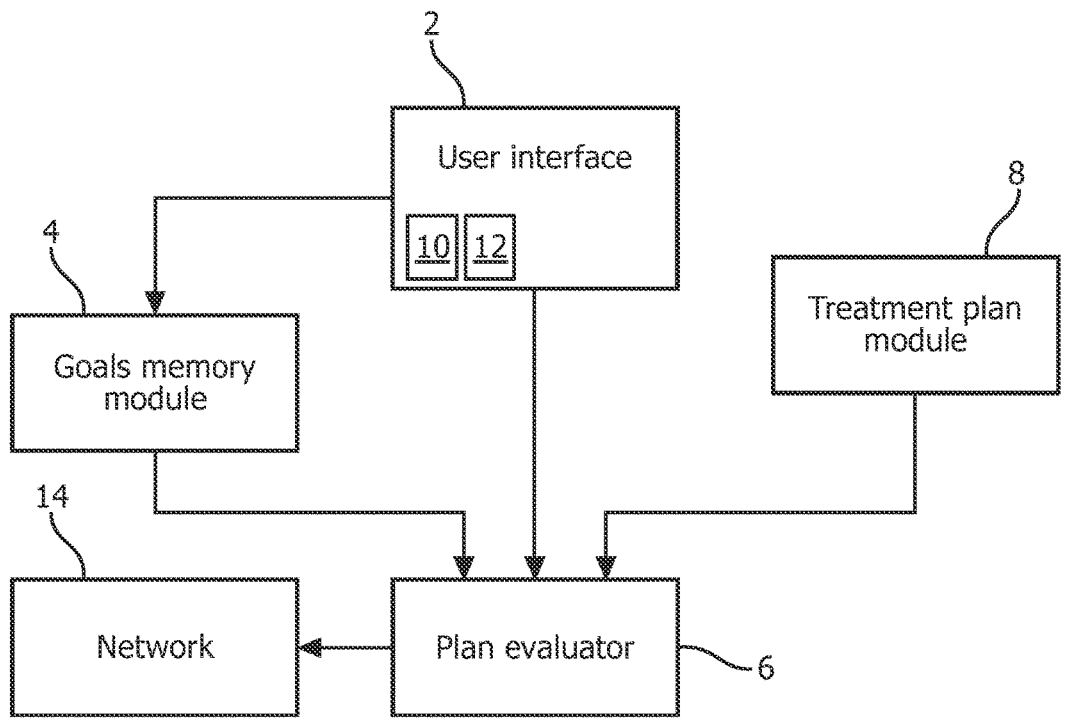
FIG. 1 depicts an embodiment of a radiation therapy plan evaluation system.

FIG. 1 depicts an embodiment of a system for evaluating a radiation therapy plan. The plan evaluation system includes a user interface 2 which accepts input from the user in terms of clinical or delivery goals. The user interface 2 accepts user input through a mouse, keyboard, touchscreen, display, microphone, data file, and the like. The user is generally an oncologist or technician with knowledge of the plan and the patient status. The user interface 2 accepts the goals from the user and stores them in a goals memory module 4. The goals memory module 4 includes a non-transitory computer readable medium which stores data and inputs. The memory module 4 accepts inputs from the user interface 2 and stores the inputs as goals data that must be accessed by a plan evaluator 6. The plan evaluator 6 includes one or more processors for accessing and processing data. The plan evaluator 6, in one embodiment, includes non-transitory computer readable media for storing instructions for the one or more processors.

The plan evaluator 6 is connected to the rest of the modules in the system. The plan evaluator 6 accesses a treatment plan residing at a treatment plan module 8 and extracts data that is relevant to plan evaluation. The plan evaluator 6 further accesses the goal memory module 4 to correlate the goals input by the user with the relevant data points that were extracted from the treatment plan. The plan evaluator 6 then correlates the data in view of the goals using a processor. The correlation links data points within the data with goals that are not met or are significant for the user to review.

Once the correlation is complete, the plan evaluator generates a report or summary of the correlated data in view of the goals and treatment plan. The plan evaluator 6 inserts markings to highlight the correlations and deviations between goals and the treatment plan data. The plan evaluator 6 constructs a report that shows different correlations that are viewable by the user.

The plan evaluator 6 is connected to a display 10. The display 10 is an LCD, TFT, LED, CRT or another screen implementation. In some embodiments, the display 10 is located within the user interface 2. The report is outputted to the display 10 from the plan evaluator 6, so that a user can view the report. After viewing the report, the user has the option of inputting further notations about the report through the user interface 2. The user, through user interface 2, can also correct any errors within the report. In the case of a correction, the plan evaluator 6 notes the correction to evolve and better evaluate future plans.

The user has the option of inputting audio notations about the report through an audio recorder 12. The audio recorder 12 includes a microphone and is connected to the plan evaluator 6, which receives the audio and attaches it to the report. In some embodiments, the audio recorder 12 is located within the user interface 2. Last, the plan evaluator 6 is attached to a network 14 over which the report can be distributed to other doctors or treatment providers for further review. For example, the report is distributed over the network 12 to the oncologist who displays and reviews the report in his/her office and sends approval, comments, corrections, and etc. back over the network 14.

Figure 2:
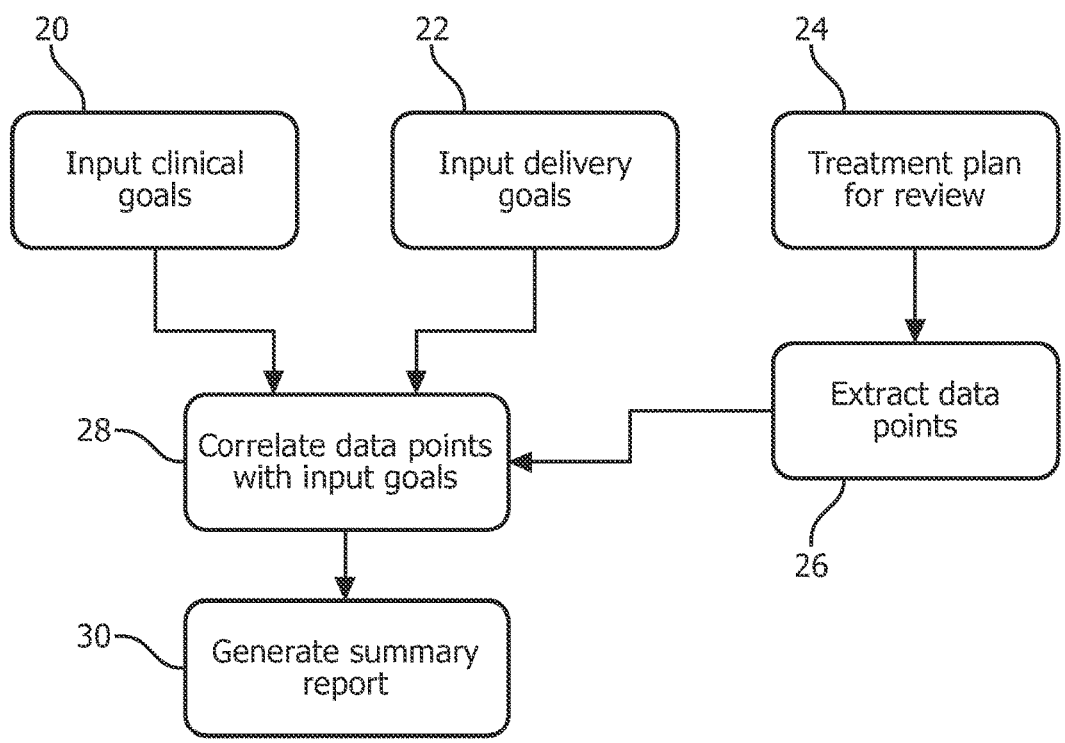
FIG. 2 depicts a flow diagram of a method to correlate data.

With reference to FIG. 2, at a step 20, clinical goals are inputted into the method. At a step 22, delivery goals can be inputted into the method by the user interface 2. The goals input include patient specific goals, pre-set goals located on a non-transitory computer readable medium, and the like. When treating a patient using IMRT or IMPT, the oncologist develops output goals for the procedure. These goals are typically clinical or delivery goals. Delivery goals correspond to the desired amount, or dosage, of radiation to be delivered to a tumor, lesion, or affected portion of the patient's body and the like. The delivery goals also include dose limits for other non-target regions of the patient, particularly organs at risk. Clinical goals are generally guidelines to be achieved during treatment. In one embodiment, the goals for dose deliverability analysis can include various indices to quantify target dose, hot and cold spot thresholds, iso-dose levels, and the like. Such goals are determined by the patient's doctor, generally an oncologist, and are reviewed by a technician to determine beam placement. It is appreciated that clinical goals and delivery goals can be inputted alone or together for evaluating the treatment plan depending on the desired evaluation sought by the user.

At a step 24, the treatment plan for review, typically located on a non-transitory computer readable medium, is input into the plan evaluator 6 for evaluation. The treatment plan can also reside in a patient's electronic health record in a remote patient record database and is accessed through the network 14. The treatment plan typically includes patient specific data from many different sources. The sources can include geometric analysis from a technician, dose distribution analysis, DVH analysis, parametric analysis, deliverability analysis and the like. Further, the treatment plan includes other patient specific data such as name, age, insurance, as well as identifiers to link the data and the plan to the patient.

The plan typically includes many different data sources unrelated to plan evaluation. The plan data is parsed for data points that are only relevant to sufficient plan evaluation. To automate finding the data points, at a step 26, using the plan evaluator 6, specific data points are extracted from the treatment plan pertaining to the geometric analysis, the dose distribution analysis, the DVH analysis, the parametric analysis, the deliverability analysis, and the like. These data points are exclusive to the plan evaluation process.

In the past, correlating data points required manual navigation between different features of the radiation treatment application. To automate the correlation, at a step 28, the extracted data points are then correlated by the plan evaluator 6 with the inputted treatment goals such that the goals are linked to the specific data points that show plan deficiencies or points of concern. The data points are compared to the goals and distinct correlations are established between the data points and the goals. The correlations typically show different views of the same data or data is related to a goal that is not met. The correlations distinctly link the data points and goals such that the link automatically shows or proves a conclusion about the plan.

Further, the plan evaluator 6 correlates the data points to one another such that similar or related information can be connected and shown in a variety of views. For example, a dose deliverability slice can show a particular area in an imaging slice adjacent an organ at risk overloaded with iso-dose lines, and the slice can be correlated to the dose volume histogram for that particular area.

At a step 30, the report that summarizes the correlations is generated by the plan evaluator 6 for the oncologist or other users to receive and digest. The report typically includes arranged slides in which the extracted data points are displayed in view of the clinical and delivery goals. The report can include warnings, annotations, visual markings to show the link between data points, or between data points and specific goals. The visual markings highlight the correlations such that the user can quickly and easily read the report.

Figure 3:
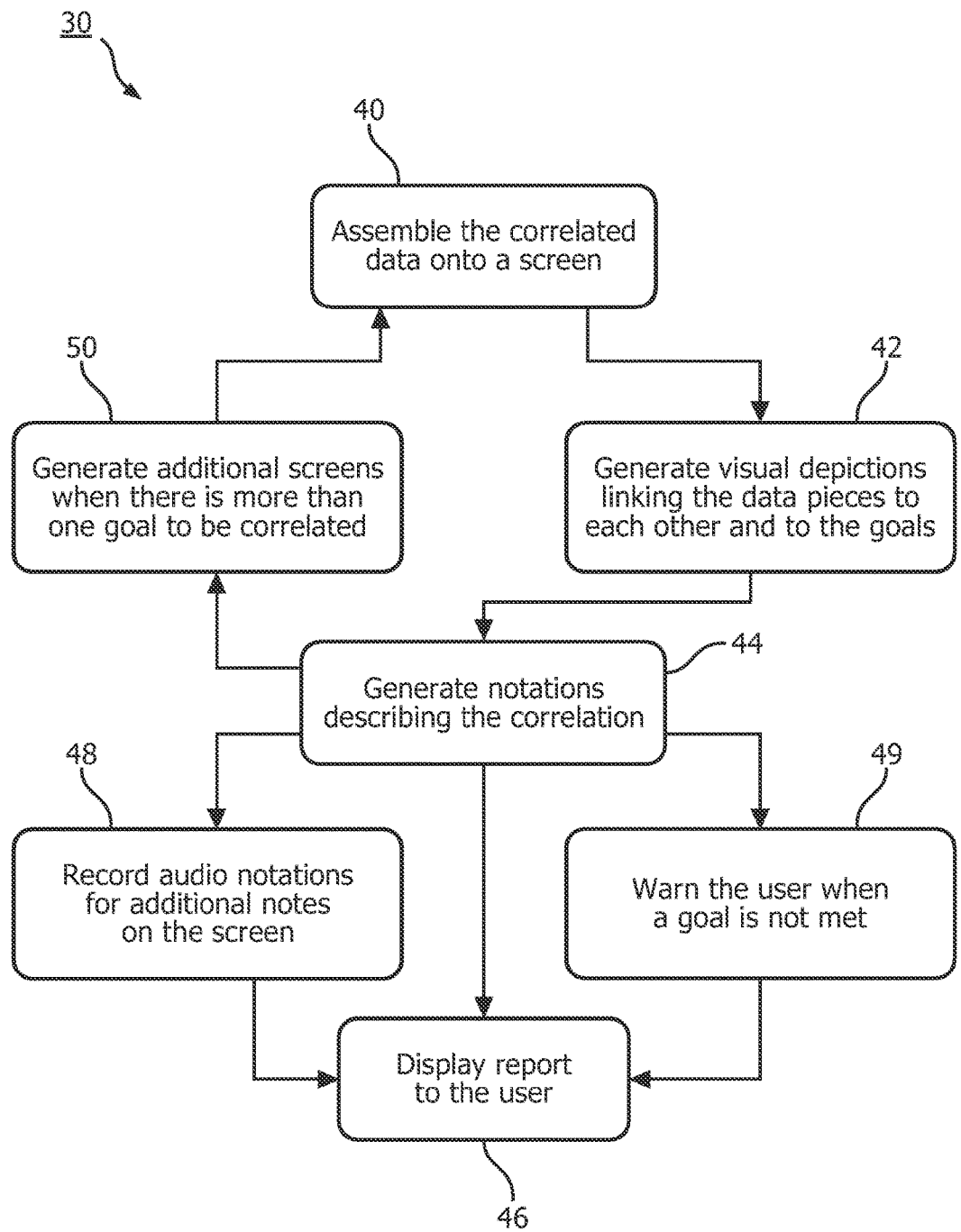
FIG. 3 depicts a flow diagram of a method to generate a final report.

The report generated through this method produces a report that is easily consumed by the user. FIG. 3 depicts a method to automate the generating step 30. At a step 40, the correlated data points from step 28, are assembled by the plan evaluator 6 and presented on a display 10 of the user interface 2. The correlated data is usually displayed together on one page or view. The data points can include imaging slices, histogram plots, and the like. The clinical or delivery goal inputs can be displayed on the same page as the correlated data points.

At a step 42, the plan evaluator 6 generates visual depictions linking the data points to each other and to the goals and inserts the depictions into the report for display on the display 10 of the user interface 2. The depictions include arrows, lines, and other indicators to distinctly point out features to be highlighted for the user. The depictions aid the user in digesting the evaluation easily and highlight specific points within the data that the user must consider when evaluating the plan.

At a step 44, notations describing the correlation between data points and goals are generated by the plan evaluator 6. Such notations interpret the correlations into a user-friendly summary that explain the correlations. Text notations are input by the plan evaluator 6 for display to the user. In one embodiment, audio notations are generated and attached to the report by the plan evaluator 6. Further, the notations include warnings to the user whenever clinical or delivery goals are not met. Such warnings are important in plan evaluation and provide a benefit of interpreting a large data set to be certain that a user does not overlook a failed goal. These notations are generated by the plan evaluator 6 automatically or input by the user through the user interface 2 after reviewing the correlated data. For example, hot spots, i.e. high delivered dose regions, adjacent an organ at risk can be marked in red. Cold spots, i.e. low delivered dose regions, in the target can be marked in blue. The slices containing the hot and cold spots can be automatically selected for display.

At a step 46, the report is displayed to the user on the display 10. The report can also be displayed on a projector, computer monitor, television, in print form, or any visual display, and the like. If the report consists of multiple screens or views, the report is shown to the user such that the user can review every screen. In some embodiments, the report can be a video clip, slideshow presentation, printed summary, data file, and the like. The present application further provides for functionality to save the report and distribute it to other consulting physicians, physicists, nurses, other medical staff, the patient, and the like.

At a step 48, the user presented with the option to record audio notations with the audio recorder 12 for additional notes after reviewing the report. The audio is attached to the report to further assist in the plan evaluation.

At a step 50, additional screens are created in some embodiments for different goals. In the case of multiple goals, it is useful to create additional screens within the report. The additional screens are created using same steps for each screen.

The generated report presents information to the user in an easily digestible format. In one embodiment, two reports are generated using the same plan information and different user inputs. The two reports are then compared to highlight differences in treating the patient due to the different inputs.

In one embodiment of the report, regions of a dose distribution map or a section of the DVH highlighted where target dose has not met an input goal (e.g. a hot or cold spot) is correlated with a patient image. Any cold spot sections are highlighted on the DVH, and on the corresponding regions in the patient image. Similarly, hot spots are highlighted on the DVH and on the corresponding patient image. Further, various quantitative indices are correlated to the DVH and patient image, and are linked to the data points.

Figure 4:
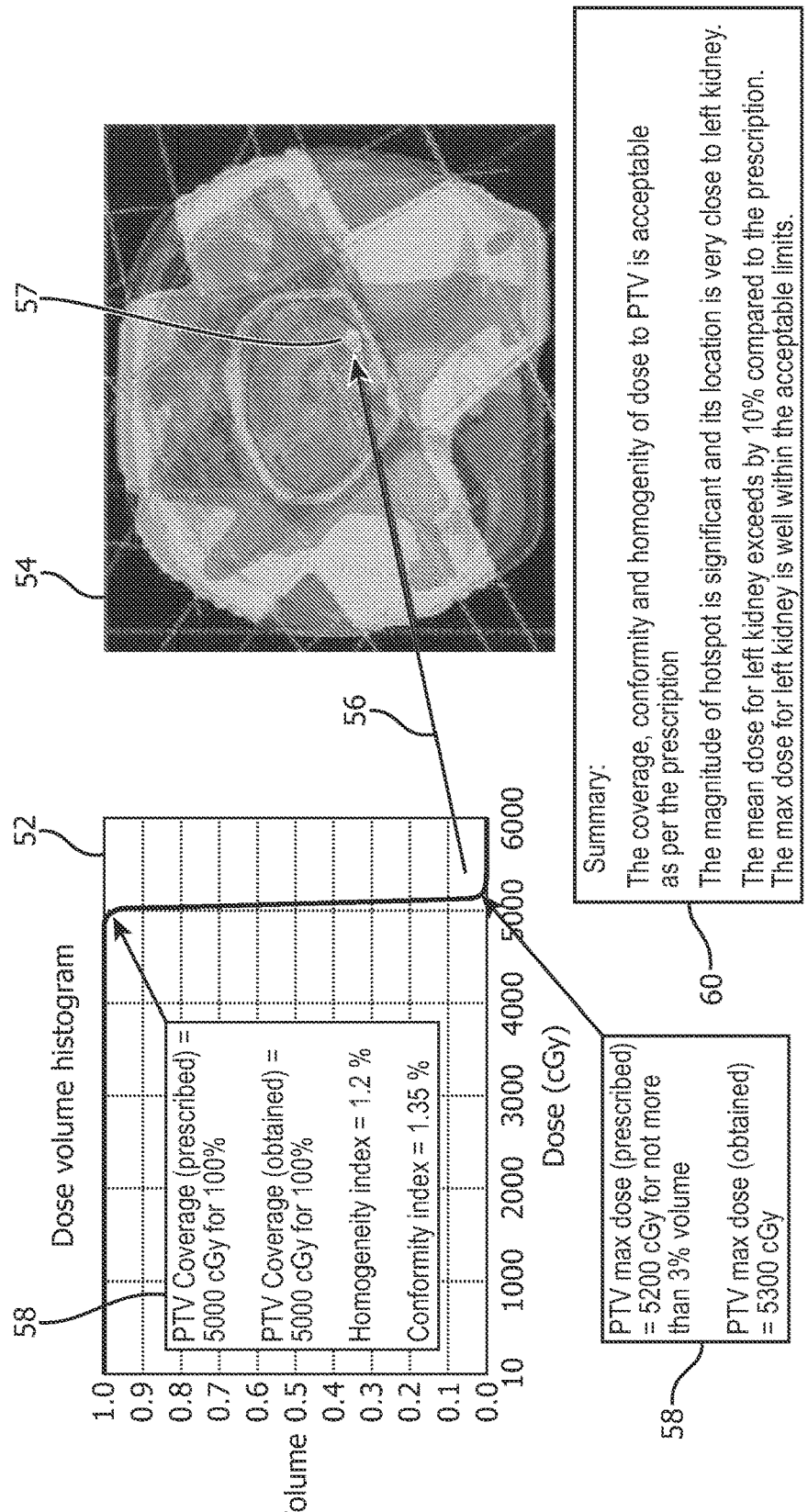
FIG. 4 depicts one embodiment of a report correlating a dose volume histogram to an imaging slice to distinctly point out the location of a dose hotspot.

FIG. 4 depicts one embodiment of a finalized report correlating a DVH curve 52 to a corresponding patient image 54 overlaid with delivered dose distributions and including the target and/or one or more organs at risk. Highlighting of important data points is depicted as a solid line 56 showing the correlation of an exceeded dose flagged by the DVH curve 52 and the image of a hot spot 57 in patient image 54. Quantitative indices 58 are displayed on the report providing further detail about important aspects of the DVH, including where sufficient radiation dosage has been met and particularly pointing out where a specified dosage limit has been exceeded. A text summary 60 is generated by the plan evaluator 6 and inserted into the report. The summary 60 describes the correlations, and further provides warnings and other information that are important to evaluation of the plan by the user.

Figure 5:
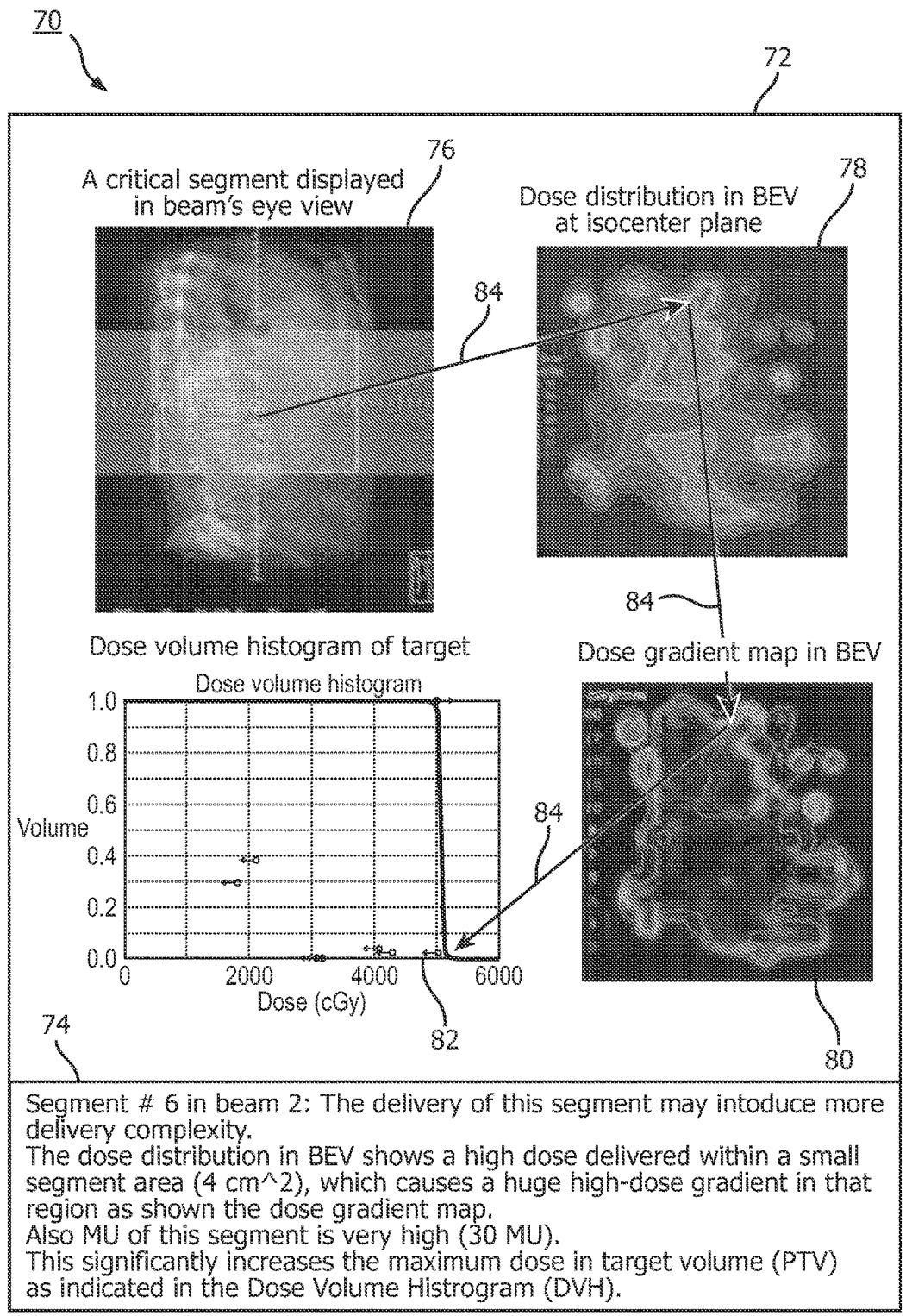
FIG. 5 depicts one embodiment of an annotated summary/report about a radiation treatment plan.

Multiple data points can be correlated and displayed together. In some embodiments, as many as four or more are displayed. FIG. 5 depicts a report 70 in which four data points are extracted and correlated to one another. The report is dissected into two regions. A data section 72 displays the correlated data points; while a notation section 74 includes text notations with commentary summarizing the correlation. Within the data section 72, a beam's eye view (BEV) patient image 76 of the target or organ at risk is displayed first. A BEV dose distribution image 78 is correlated with the patient image 76. The dose distribution 78 is correlated with the patient image 76 such that it shows the amount of radiation at the isocenter plane of one of the organs at risk shown in the patient image 76. The high dose outside of the planned target volume (PTV) is at the expense of dose to the target region in the PTV. The two images each supply different data to the user about the same organ at risk or target that is irradiated. The dose distribution 78 is then correlated with a BEV dose gradient map 80 based off the dose distribution 78. A dose gradient map 80 further supplies information about the treatment plan that shows the rate of dose increase, and is linked to the dose distribution 78. A dose volume histogram 82 of the irradiated anatomical region is correlated to the other images. In the illustrated example, the report points out a region that shows a particularly high dose with a high dose gradient. Highlights on the images, e.g. arrows 84, distinguish the region to bring the oncologist's or user's attention to a potential area of concern that is useful in the plan evaluation. Without the report, the user would typically manually search through the entire plan data to find each data point, and subsequent related data points, and the particular segment within the data points. The user would then correlate each data point manually. The method and system of the present application automates this part of the evaluation process.

Figure 6:
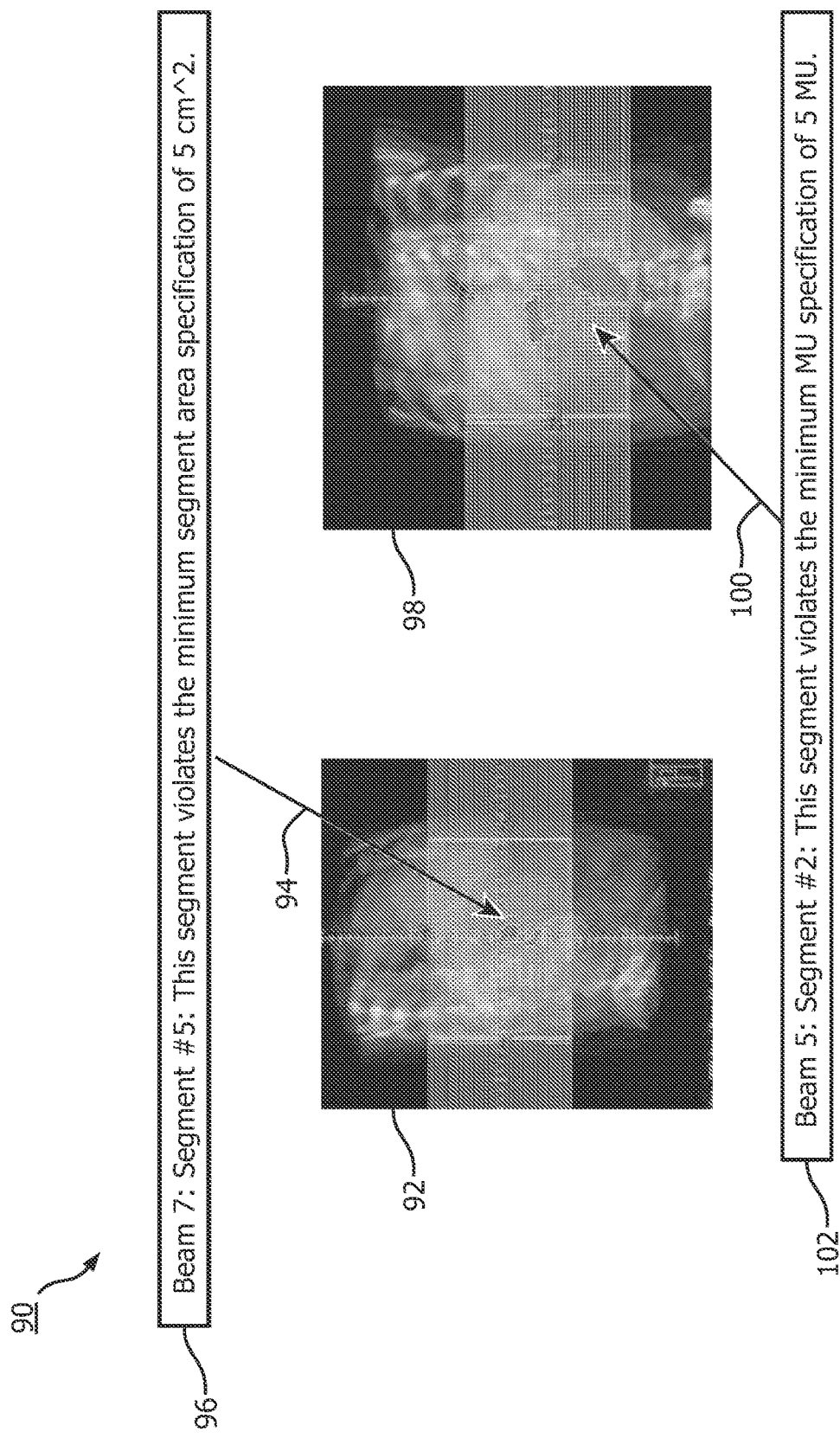
FIG. 6 depicts one embodiment of a report of deliverability inputs correlated to segment quality.

During plan evaluation, a warning to the user is beneficial when a goal or threshold is exceeded. A user might overlook certain details within the large dataset when conducting a manual plan evaluation, especially with multiple beams each having imaging segments to be reviewed. With reference to FIG. 6, distinct warnings are shown in the report 60. In this case, the warnings can be compiled on a separate screen within the report, when different warnings are presented to the user. The different warnings arise from two distinct data points. In a patient image 92, a distinct region violates a minimum dose specification along one of the radiation beams. An area of concern is highlighted with arrow 94. The evaluation process determined that the highlighted segment violates the minimum segment area specification. A warning 96, describes the violating segment to the user. Juxtaposed with the patient image 92 is another image 98 of the patient from a differently angled view along a trajectory of the radiation beam in another segment of the RTP. A region of concern is highlighted with an arrow 100, where the evaluation process has determined that the segment violates the minimum monitor unit specification. A warning 102, describes the violating segment to the user.

The methods, and system according to the present application are not only applicable to plan evaluation of radiation or proton therapy plans, but e.g. as well in other systems or environments which are subject when providing patient care. Other than oncologists, physicists, and other treatment providers, the present application is of particular use as a training tool to train users to evaluate plans, while providing a check on the users in case a part of the plan is overlooked.

Although the system and method of the present disclosure have been described with reference to exemplary embodiments thereof, the present disclosure is not limited to such exemplary embodiments. Rather, the system and method disclosed herein are susceptible to a variety of modifications, enhancements and/or variations, without departing from the spirit or scope hereof. Accordingly, the present disclosure embodies and encompasses such modifications, enhancements and/or variations within the scope of the claims appended hereto.

The invention claimed is:

1. A method for evaluating treatment plans for delivering radiation therapy to a patient, the method comprising:
   receiving a treatment plan, the treatment plan including patient specific data, the patient specific data including a dose volume histogram and a dose distribution;
   receiving evaluation parameters for the treatment plan;
   extracting evaluation data from the patient specific data based on the evaluation parameters;
   correlating the evaluation data with the evaluation parameters to provide correlated data including a plurality of correlations and a plurality of deviations;
   generating a summary associated with the treatment plan for display on a screen, the summary presenting the correlated data wherein the correlations and the deviations are highlighted; and
   generating audio notations explaining the correlations in the generated summary;
   wherein the extracting and correlating include:
      evaluating the dose volume histogram and dose distribution to identify hot or cold spots; and
      associating the hot or cold spots with the dose volume histogram and the dose distribution.

2. The method according to claim 1, wherein generating the summary includes:
   assembling the correlated data onto a screen within the summary;
   generating visual depictions
   linking the correlated data to each other and to the evaluation parameters within the screen;
   displaying the screen on a display as part of the summary with treatment plan and the highlighted correlations and deviations in the summary.

3. The method according to claim 1, wherein generating the summary includes:
   warning a user when the received evaluation parameters are not satisfied by the treatment plan.

4. The method according to claim 1, wherein the patient specific data further includes at least one of: geometric analysis data, parametric analysis data, and deliverability analysis data of a patient.

5. The method according to claim 1, wherein the generated summary includes:
    displaying the dose volume histogram and the dose distribution.

6. The method according to claim 1, wherein generating the summary includes:
    generating text notations describing the correlations between the correlated data and evaluation parameters onto the screen.

7. A non-transitory computer readable medium carrying software for controlling one or more processors to perform the method according to claim 1.

8. A system for evaluating a radiation treatment plan, the system including:
    a user interface configured to receive an input from a user;
    a plan evaluator including one or more processors programmed to:
        receive a treatment plan, the treatment plan including patient specific data;
        receive evaluation parameters input through the user interface for the treatment plan;
        extract evaluation data points from the patient specific data according to the evaluation parameters;
        correlate the evaluation data with the evaluation parameters to provide correlated data including correlations and deviations; and
        generate a summary associated with the treatment plan, the summary presenting the correlated data with highlighting between the correlations and deviations; and
    a display configured to display the summary and generated text notations describing the correlations between the correlated data and evaluation parameters onto the display.

9. The system according to claim 8, wherein the plan evaluator, when generating the summary, is programmed to:
    assemble the correlated data onto a screen within the summary;
    generate visual depictions that link the correlated data to each other and to the evaluation parameters within the screen including the highlighted correlations and deviations; and
    display the screen on the display as part of the summary.

10. The system according to claim 8, wherein the plan evaluator, when generating the summary, is programmed to:
    generate a warning to the user when the captured evaluation parameters are not satisfied by the treatment plan.

11. The system according to claim 8, wherein the treatment plan includes at least one of: geometric analysis data, a dose distribution analysis data, dose volume histogram data, parametric analysis data, or deliverability analysis data of a patient.

12. The system according to claim 8, wherein the one or more plan evaluator processors is programmed to extract the data points located in the evaluation parameters data by:
    evaluating a dose volume histogram located in the evaluation parameters data for hot or cold spots;
    evaluating a dose distribution plot to locate the hot or cold spots; and
    associating the dose distribution plot with the dose volume histogram.

13. The system according to claim 12, wherein the one or more plan evaluator processors is further programmed to control the display to display the dose distribution plot and the dose volume histogram together within the generated summary on the display.

14. The system according to claim 8, wherein the one or more plan evaluator processors is further programmed to generate audio notations and associates the audio notations with the summary.

15. A method for reviewing a treatment plan for delivering radiation therapy to a patient, the method comprising:
    receiving a treatment plan, the treatment plan including geometric analysis data, a dose distribution analysis data, dose volume histogram data, parametric analysis data, and deliverability analysis data of a patient;
    identifying a plurality of clinical goals for the treatment plan;
    identifying a plurality of delivery goals for the treatment plan;
    extracting goal data points from the treatment plan;
    correlating the goal data points to identify deficiencies in the treatment plan; and
    generating a first report to display the correlated data points using visual markings to highlight identified deficiencies.

16. The method according to claim 15, wherein the first report includes a video clip showing different screens in succession representing multiple correlations.

17. A system, including one or more processors programmed to perform the method according to claim 15, wherein the first report is transmitted over a network.

18. The method according to claim 15, further including:
    generating a second report using at least one different clinical goal of the plurality of clinical goals; and
    comparing the second report to the first report to highlight differences in delivering radiation therapy to the patient.

* * * * *